United States Patent
Sansur et al.

(10) Patent No.: US 10,765,525 B2
(45) Date of Patent: Sep. 8, 2020

(54) INTERBODY CAGE WITH SPILL-FREE BIOLOGICAL MATERIAL COMPARTMENT

(71) Applicant: University of Maryland, Baltimore, Baltimore, MD (US)

(72) Inventors: Charles Sansur, Towson, MD (US); Steven C. Ludwig, Baltimore, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 0 days.

(21) Appl. No.: 16/047,473

(22) Filed: Jul. 27, 2018

(65) Prior Publication Data

US 2019/0053910 A1 Feb. 21, 2019

Related U.S. Application Data

(60) Provisional application No. 62/537,610, filed on Jul. 27, 2017.

(51) Int. Cl.
*A61F 2/44* (2006.01)
*A61F 2/30* (2006.01)
*A61F 2/28* (2006.01)
*A61F 2/46* (2006.01)

(52) U.S. Cl.
CPC .......... *A61F 2/441* (2013.01); *A61F 2/30744* (2013.01); *A61F 2/30771* (2013.01); *A61F 2/447* (2013.01); *A61F 2/4455* (2013.01); *A61F 2/4465* (2013.01); *A61F 2002/2835* (2013.01); *A61F 2002/3092* (2013.01); *A61F 2002/3093* (2013.01); *A61F 2002/30387* (2013.01); *A61F 2002/30471* (2013.01); *A61F 2002/30476* (2013.01); *A61F 2002/30522* (2013.01); *A61F 2002/30578* (2013.01); *A61F 2002/30581* (2013.01); *A61F 2002/30589* (2013.01); *A61F 2002/30593* (2013.01); *A61F 2002/30784* (2013.01); *A61F 2002/30904* (2013.01); *A61F 2002/30909* (2013.01); *A61F 2002/4629* (2013.01)

(58) Field of Classification Search
CPC ................................................ A61F 2/44–447
USPC ........................................... 623/17.11–17.16
See application file for complete search history.

(56) References Cited

U.S. PATENT DOCUMENTS

| | | | |
|---|---|---|---|
| 5,609,635 A | 3/1997 | Michelson | |
| 6,264,656 B1 | 7/2001 | Michelson | |
| 6,302,914 B1 | 10/2001 | Michelson | |
| 8,585,766 B2 * | 11/2013 | Ullrich, Jr. ............. | A61F 2/447 623/17.11 |
| 8,715,355 B2 | 5/2014 | Kleiner | |
| 9,427,328 B2 | 8/2016 | Drochner et al. | |
| 2002/0116066 A1 | 8/2002 | Chauvin et al. | |
| 2003/0040802 A1 * | 2/2003 | Errico ..................... | A61F 2/442 623/17.14 |

(Continued)

*Primary Examiner* — Nicholas J Plionis
(74) *Attorney, Agent, or Firm* — Wenderoth, Lind & Ponack, L.L.P.

(57) ABSTRACT

Interbody cages for spinal stabilization having a frame that surrounds a central compartment suitable for retaining biological material, such as bone graft material. The central compartment acts as a spill-free bone and biologic compartment that allows a surgeon to introduce the interbody cage into the body in an effective manner without spilling the biological material. Methods for introducing the interbody cages are disclosed.

4 Claims, 14 Drawing Sheets

(56) References Cited

U.S. PATENT DOCUMENTS

| | | | |
|---|---|---|---|
| 2003/0187506 A1* | 10/2003 | Ross | A61F 2/442 623/17.13 |
| 2004/0034430 A1 | 2/2004 | Falahee | |
| 2004/0093088 A1* | 5/2004 | Ralph | A61F 2/442 623/17.14 |
| 2004/0127990 A1* | 7/2004 | Bartish, Jr. | A61F 2/4465 623/17.11 |
| 2005/0085913 A1* | 4/2005 | Fraser | A61B 17/7059 623/17.11 |
| 2005/0256579 A1* | 11/2005 | Keller | A61F 2/4425 623/17.15 |
| 2007/0255416 A1* | 11/2007 | Melkent | A61F 2/4465 623/17.16 |
| 2009/0198339 A1* | 8/2009 | Kleiner | A61F 2/446 623/17.16 |
| 2011/0190888 A1* | 8/2011 | Bertele | A61F 2/30907 623/17.11 |
| 2013/0110238 A1* | 5/2013 | Lindemann | A61F 2/30744 623/17.12 |
| 2013/0218276 A1* | 8/2013 | Fiechter | A61F 2/4455 623/17.16 |
| 2015/0250607 A1* | 9/2015 | Drochner | A61F 2/4455 623/17.16 |

* cited by examiner

INTERBODY CAGE WITH SPILL-FREE BIOLOGICAL MATERIAL COMPARTMENT

TECHNICAL FIELD

The present application generally relates to interbody cages for spinal stabilization. More specifically, the present application relates to interbody cages for spinal stabilization with one or more spill-free, biological material compartments.

BACKGROUND

During spinal fusion procedures, a solid bridge is typically formed between the two vertebral segments to limit movement in the section of the spine of the spinal fusion. A common technique for spinal fusion procedures involves the use of interbody cages to fill the gap between the two segments in the spine that are being fused. The addition of bone graft material during the spinal fusion procedure can additionally provide a suitable foundation and environment that allows new bone growth and fuses the area of the procedure over time. Interbody cages can have central cavities that can be packed with bone graft materials. However, packing these central cavities tightly with such material can be difficult because the bone graft materials can fall out of the interbody cage while setting the interbody cage into place since, for example, force can be required to insert the interbody cage into the body.

Others have attempted to solve these problems by constructing interbody cages that are configured to retain bone graft material during spinal fusion procedures. For instance, in U.S. Pat. No. 5,609,635, the disclosed lordotic implant provides a solid cage with a sliding door on the rear face of the device. Even though the configuration disclosed by U.S. Pat. No. 5,609,635 improves upon standard interbody cages, the disclosed lordotic implant has several disadvantages. One example of a disadvantage is that the top and bottom faces of the device are rigid, and thus the disclosed lordotic implant does not allow for maximum graft packing due to the rigidity of the cage. Another disadvantage is that the sliding door of the lordotic implant is located on the rear face of the cage making it difficult to firmly pack the cavity since, for example, additional bone grafting material cannot be easily added to the cage after insertion into the body.

Another attempt to address the above-mentioned problems is described in U.S. Pat. No. 8,715,355, wherein a three-sided cage, with removable plates for top and bottom faces is disclosed. Once inserted between two vertebral bodies, the central cavity is packed with bone graft materials. The top and bottom plates can be removed, and the rear face is covered to contain the graft materials. However, the cavity in the disclosed configuration is difficult to pack tightly. Moreover, the surgeon inserting the disclosed cage in the body faces difficulty in determining the total amount of grafting material that should be inserted into the patient before the rear opening is closed.

Even further, packing the cage after insertion can cause problems since the cage may migrate from the desired location. If such migration occurs, a greater risk to the nerves and/or surrounding anatomy exists when packing the cage after insertion since these structures may be inadvertently damaged during the packing process. Accordingly, the known techniques and, devices for spinal fusion procedures have a number of problems.

BRIEF SUMMARY

In view of the above-mentioned exemplary problems with conventional and known interbody cages, the present application provides interbody cages having a spill-free, biological material compartment, and further provides associated methods for using the disclosed interbody cages.

One aspect of the present application includes an interbody cage for spinal stabilization comprising a) a frame that surrounds a central compartment the frame comprising a top face and a bottom face, the top face comprising one or more top openings, and the bottom face comprising one or more bottom openings, b) a cover that covers the one or more bottom openings, the cover comprising one or more apertures suitable for retaining biological material, and c) a removable cover configured to be removably secured to the top face of the frame such that the removable cover covers the one or more top openings when secured to the top face of the frame, the removable cover comprising one or more apertures suitable for retaining biological material, wherein the top face of frame is configured to receive the removable cover.

In another aspect, at least one of the cover and the removable cover comprises mesh.

In another aspect, at least one of the cover and the removable cover comprises flexible mesh.

In another aspect, at least one of the cover and the removable cover is convex.

In another aspect, the frame further comprises at least one vertical face, wherein the at least one vertical face comprises one or more apertures suitable for retaining biological material.

In another aspect, the at least one vertical face comprises mesh.

In another aspect, at least one of the top face and the bottom face comprises teeth that extend in an outward direction.

In another aspect, the frame is configured to receive an insertion rod.

In another aspect, at least one of the cover and the removable cover further comprises a pivotable attachment mechanism configured to engage at least one of the top face and the bottom face.

Another aspect of the present application includes an interbody cage for spinal stabilization comprising a) a frame that surrounds a central compartment, the frame comprising a top face and a bottom face, the top face comprising one or more top openings, and the bottom face comprising one or more bottom openings, b) a cover that covers the one or more bottom openings, the cover comprising one or more apertures suitable for retaining biological material, and c) an openable cover configured to be secured to the top face of the frame in a closed position and capable of being opened, the openable cover covering the one or more top openings when secured to the top face of the frame in the closed position, the removable cover comprising one or more apertures suitable for retaining biological material.

In another aspect, the openable cover is configured to be secured to the top face of the frame by at least one latching mechanism and at least one hinge.

In another aspect, at least one of the cover and the openable cover comprises mesh.

In another aspect, at least one of the cover and the openable cover comprises flexible mesh.

In another aspect, at least one of the cover and the openable cover is convex.

In another aspect, the frame further comprises at least one vertical face, wherein the at least one vertical face comprises one or more apertures suitable for retaining biological material.

In another aspect, the at least one vertical face comprises mesh.

In another aspect, at least one of the top face and the bottom face comprises teeth that extend in an outward direction.

In another aspect, the frame is configured to receive an insertion rod.

In another aspect, at least one of the cover and the openable cover further comprises a pivotable attachment mechanism configured to engage at least one of the top face and the bottom face.

Other objects, features and advantages of the present invention will be apparent to those of ordinary skill in the art in view of the following detailed description of the invention and accompanying drawings.

BRIEF DESCRIPTION OF THE DRAWINGS

The drawings as provided for herein set forth some exemplary embodiments of the interbody cages for spinal stabilization and methods of the present application, the detailed description of which follows. The drawings are merely exemplary, and are clearly not intended to limit the invention.

DETAILED DESCRIPTION

The interbody cages for spinal stabilization and methods of the present application are now described by reference to the embodiments. The description provided herein is not intended to limit the scope of the claims, but to exemplify the variety encompassed by the present application. The embodiments are described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

Figure 1A:
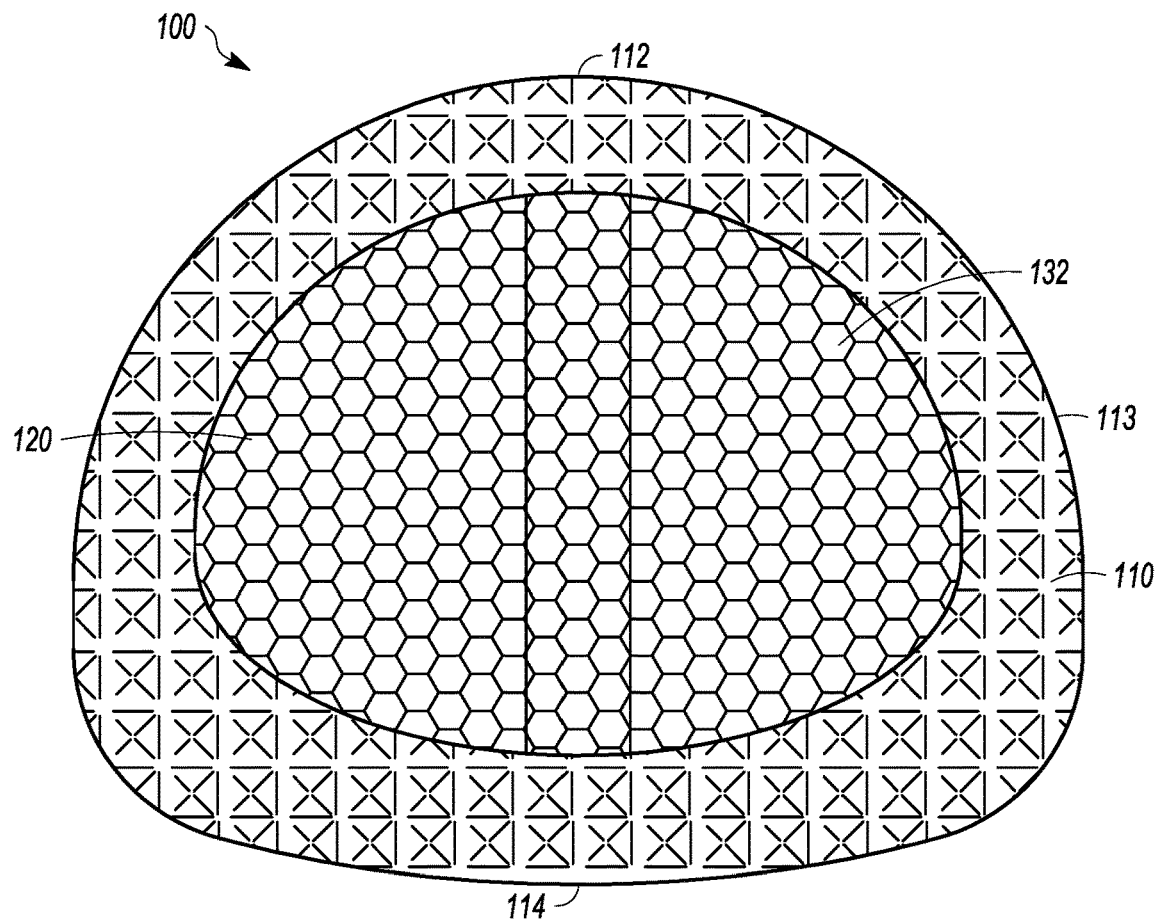
FIG. 1A is a planar view of one embodiment of the interbody cage.
Figure 1B:
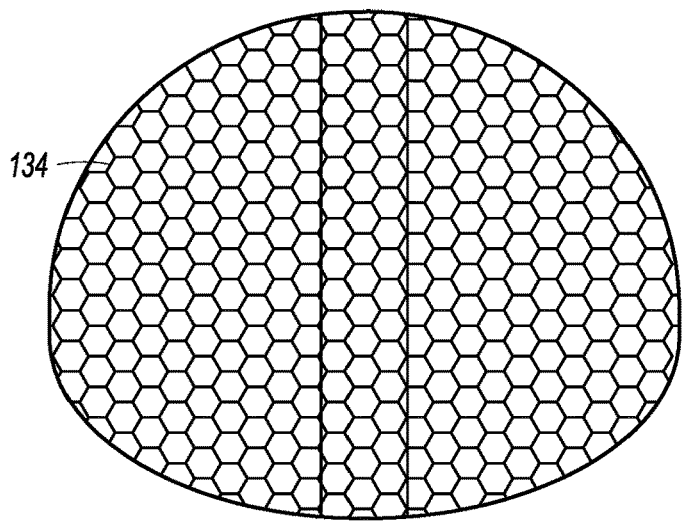
FIG. 1B is a planar view of a removable cover that is mesh for the intervertebral cage of FIG. 1A.
Figure 1C:
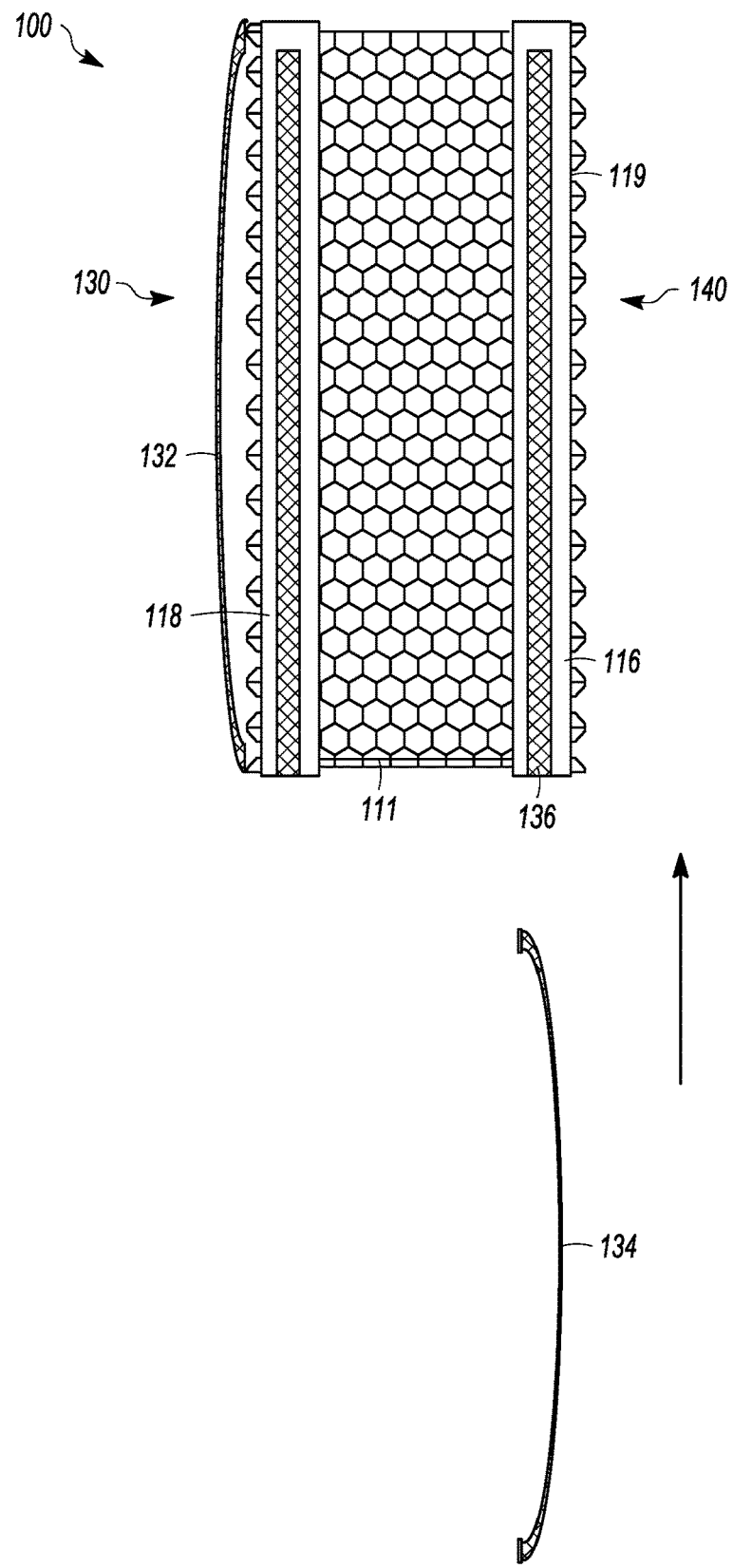
FIG. 1C is an elevation view of the intervertebral cage of FIG. 1A.

FIGS. 1A and 1C show an interbody cage 100 for spinal stabilization with a spill-free, biologic material compartment. The biological material can include, but is not limited to, bone grafting material selected from one or more of autograft, allograft, demineralized bone matrix, ceramic bone extenders, stem cells, crushed cancellous allograft bone, and collagen sponge containing bioactive material, such as bone morphogenetic protein. However, the biological materials can include. The interbody cage 100 is configured to contain biological material, such as bone grail material, therein and also support the spine of a patient. Furthermore, the interbody cage 100 is configured to receive biological material, such as bone graft material, without the need for additional special equipment and having the ability to remain secured when placed into the interbody spinal space of a patient.

The interbody cage 100 for spinal stabilization has a frame 110 that extends around the perimeter of the interbody cage 100 and surrounds a central compartment 120. As seen in FIGS. 1A and 1C, the frame 110 can have a vertical face 111, wherein the vertical face 111 can have at least a front face 112, side faces 113, and a rear face 114. Each of the front face 112, the side faces 113, and the rear face 114 may be separated by one or more edges similar to the embodiment shown in FIGS. 4 to 8, or may be configured to be one contiguous curved body as illustrated in FIGS. 1A and 1C. Alternatively, the vertical face 111 can include a combination of one or more edges and one or more curves. In the exemplary embodiment shown in FIGS. 1A and 1C, the front face 112 is configured to substantially fill a gap between two vertebral bodies, such that the front face 112 may have a curvature and thickness greater than a curvature and thickness of rear face 114. Alternatively, the front Thee 112 may have a curvature and thickness less than a curvature and thickness of rear face 114. In the embodiment shown in FIG. 1A, the front face 112 and the rear face 114 have substantially the same thickness such that the angle therebetween is 0°. The actual angle will be determined based upon the location of the spinal fusion and the degree necessary for the spinal fusion. Angulation of interbody cage 100 can be determined based upon typical human morphometric angularities of the disc space, and based on the goals of the spine surgeon for the correction of a spinal deformity. The frame 110 can be made of rigid material that is suitable to withstand the compressive forces of the spine when fully loaded. The side faces 113 can be generally be rigid and solid, and can join the front face 112 to the rear face 114.

At least a portion of the vertical face 111 of frame 110 can be open to allow for new bone growth into central compartment 120. In the illustrated embodiment shown in FIG. 1C, the vertical face 111 includes mesh. The mesh of the vertical face 111 can be rigid, or can be flexible to enable an additional volume of bone graft material to be placed inside the central compartment 120. In other embodiments, the vertical face 111 is made of a rigid material having one or more openings that are larger than what is provided by the mesh.

The frame 110 can have a top face 116 and a bottom face 118. The top face 116 and the bottom face 118 can be generally flat, but may have one or more teeth 119 extending outward from the top face 116 and/or the bottom face 118, respectively, as seen in FIG. 1C. The teeth 119 can be configured to prevent slippage of the interbody cage 100 once the interbody cage 100 is inserted into the body. The surfaces the interbody cage 100 can have a prefabricated texture to facilitate osseointegration. Furthermore, ridges on surface of the cage where endplates are located prevent the cage from backing out. The bottom face 118 can have one or more bottom openings 130 that open the central compartment 120 to the vertebral body below the interbody cage 100. Each of the one or more bottom openings 130 can have a cover 132, which can be removable from the interbody cage 100 or can be secured to the interbody cage 100. The cover 132 can be partially or entirely mesh. A single cover 132 can cover one, some, or all of the one or more bottom openings 130. The cover 132 can have mesh pores that are configured to retain the graft material in the central compartment 120 and to enable bone growth into the middle of the interbody cage 100. The mesh pores can have a diameter that is small enough to retain the graft material within the cage 100 and large enough to allow bone growth through the cover 132.

In the illustrated embodiment of FIGS. 1A and 1C, a single bottom opening 130 is shown, but other embodiments may have two, three, four, or more separate openings 130. The cover 132 may be flat or convex. The cover 132 can be generally pliable to frictionally fit into the space between the vertebral bodies. The cover 132 can also be convex to maximize the amount of graft material that can be packed into the central compartment 120. Furthermore, the convex shape of the cover 132 can generally flatten when pressure is applied, such as when the weight of a patient compresses the interbody cage 100 when fully loaded into adjacent vertebral bodies. The interbody cage 100 can also be convex to maximize the amount of grafting material that can be packed into the central compartment, while providing greater contact with concave endplates of the vertebrae. The convex shape can also be compressible to allow for temporary compression during insertion process with re-expansion onto the concave endplates of the adjacent vertebrae when in the final position.

The cover 132 thickness can be uniform or non-uniform to provide flexibility and/or strength of the cover 132. For example, the cover 132 may be thinner at an apex of convexity to allow for flexibility, and the cover 132 may be thicker near the outer frame 110 that extends around the perimeter of the interbody cage 100 to strengthen the cover 132 and ease insertion of the cover 132 into the sliding groove of interbody cage 100. The mesh pores of each of the meshes discussed herein can be about 2 mm wide, and the mesh material can have a thickness of between approximately 1 mm and 2.5 mm. Further, the mesh pores may have diameters of between approximately 0.5 mm and 10 mm in width. The thickness of the cover 132 may be between approximately 0.1 mm and 5 mm.

The top face 116 can have one or more top openings 140 that open the central compartment 120 to the vertebral body above the interbody cage 100. The top face 116 can be configured to receive a removable cover 134, which can be generally similar to cover 132. The removable cover 134 can be partially or entirely mesh. The removable cover 134 can include a frame surrounding the perimeter thereof such that the frame of the removable cover 134 can create a base lattice for the removable cover 134 and be helpful to help engage the channel 136. In the illustrated embodiment of FIG. 1C, the removable cover 134 is configured to slide into channel 136 on the outer surface of top face 116. A locking mechanism can be used to secure the cover 134 into place in the channel 136. For instance, a clamp could be inserted into the channel 136 to prevent the removable cover 134 from exiting the channel 136. However, other locking mechanisms can be appropriately used, such as one or more screws, pins, adhesives, etc. The removable cover 134 may be flat or may be convex to maximize an amount of grafting material that can be packed into central compartment 120, and to increase flexibility and/or strength of the removable cover 134, as described above. The convexity of the removable cover 134 can be predetermined such that the removable cover 134 can be manufactured to have a desired convexity.

Figure 1D:
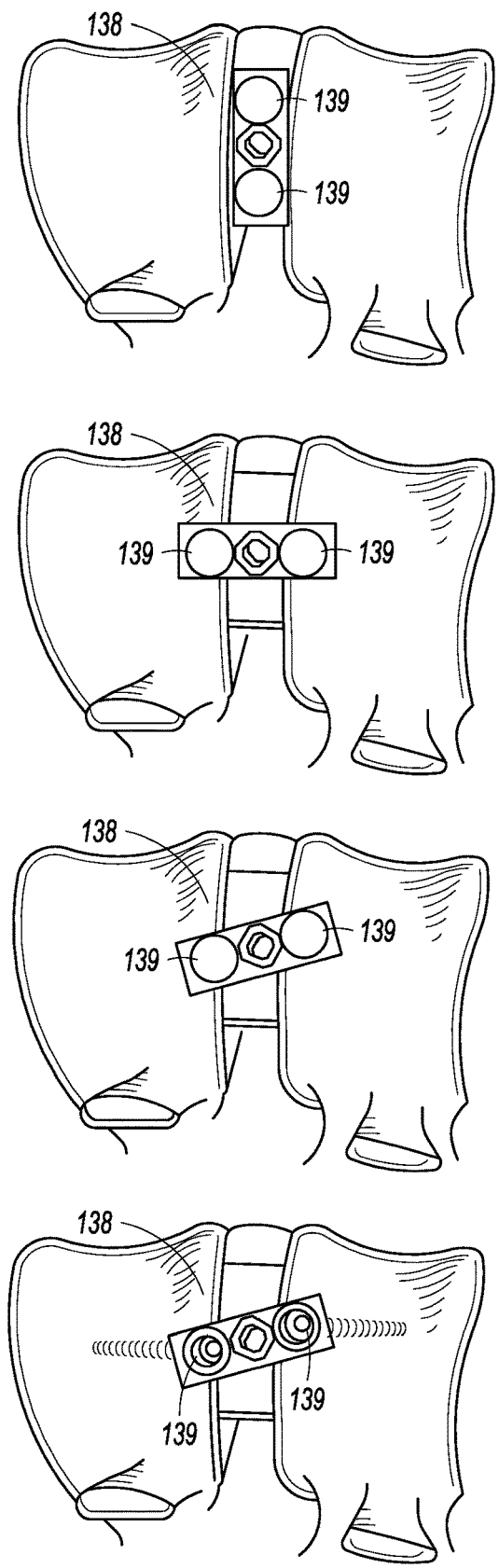
FIG. 1D is a series of side views of an interbody cage inserted between vertebral members and having a pivotable attachment mechanism.

The present application is not limited to an embodiment wherein the removable cover 134 is configured to slide into channel 136 on the outer surface of top face 116. The removable cover 134 can be secured to the top face by alternative methods. For instance, as seen in FIG. 1D, an attachment mechanism 138 can be located on an outer surface of the removable cover 134 and can be configure to pivot. The attachment mechanism 138 can have one or more arms that are configured to engage, for example, one or more channels on the top face 116 when the attachment mechanism is pivoted. In such an embodiment, the removable cover 134 could be placed onto the top face 116 with the attachment mechanism 138 pivoted so that the attachment mechanism 138 does not interfere with the placement of the removable cover 134. Once the removable cover 134 is placed onto the top face 116, the attachment mechanism 138 could pivot to engage the top face 116, thereby securing the removable cover 134 to the frame. For instance, the top face 116 and the attachment mechanism 138 could have interlocking channels that engage when the attachment mechanism is pivoted to engage the top face 116. The attachment mechanism 138 could be centrally located on the removable cover 134 such that the arms of the attachment mechanism 138 can be substantially the same length, and engage the interlocking channels on substantially opposite sides of the top face 116 when the attachment mechanism 138 is pivoted. Alternatively, the attachment mechanism 138 could be non-centrally located on the removable cover 134 such that the arms of the attachment mechanism can be different lengths, and engage the interlocking channels on different sides of the top face 116 when the attachment mechanism 138 is pivoted. Even further, the attachment mechanism 138 can be additionally secured to the frame via a locking mechanism, such as one or more screws, pins, adhesive, etc. Alternatively, the attachment mechanism 138 can be located on the cover 132 and can be used with additional embodiments discussed below, including on the openable cover 236.

The attachment mechanism 138 can also extend beyond the top face 116 such that the attachment mechanism can be secured to one or more vertebral bodies. In such an embodiment, the portion of the attachment mechanism 138 that extends beyond the top face 116 could have one or more apertures 139 therein to secure such a portion to the vertebral body via a locking mechanism, such one or more of screws, pins, adhesives, etc., as seen in FIG. 1E. The one or more aperture 139 can also be countersunk to provide a substantially smooth surface on the faces of the attachment mechanism when secured to one or more vertebral bodies.

The top face 116 can have one or more top openings 140 that open the central compartment 120 to the vertebral body above the interbody cage 100. The removable cover 134 can cover one or more of the one or more top openings 140. In the illustrated embodiment of FIGS. 1A and 1C, a single top opening 140 is shown, but other embodiments may have two, three, four, or more separate top openings 140.

In the embodiment illustrated in FIGS. 1A and 1C, the central compartment 120 is one space. However, in other embodiments, the central compartment 120 can be divided into two, three, four, or more compartments. Support structures may extend across the vertical face 111 and through the central compartment 120. Such structural supports can increase the load capacity of the cage 100, when necessary, and/or may also provide additional surface area for bone growth and integration through the interbody cage 100. The structural supports can be solid and/or may include one or more apertures therein.

Figure 2:
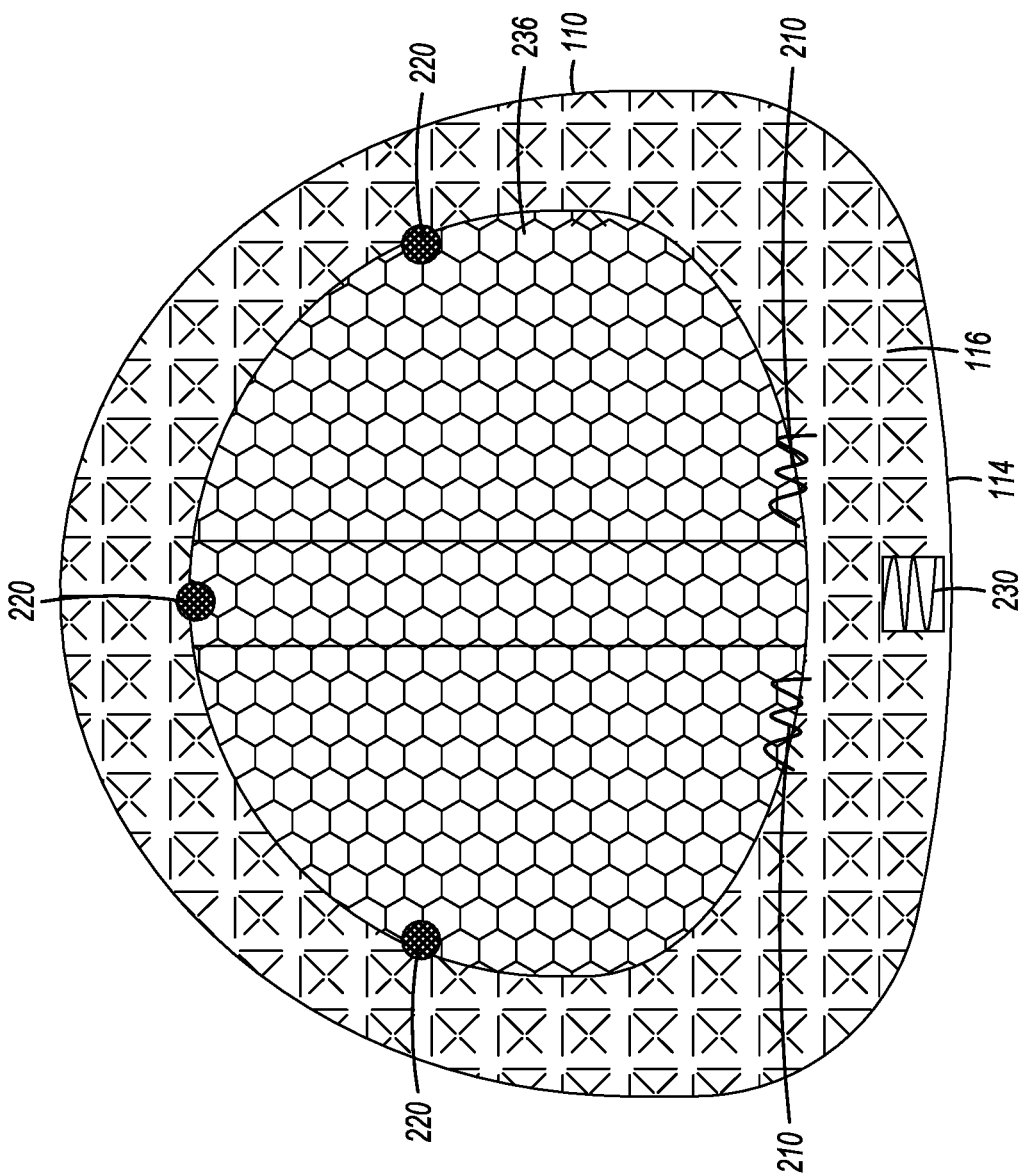
FIG. 2 is a planar view of another embodiment of the interbody cage.

FIG. 2 illustrates another embodiment of an interbody cage 100. As seen in FIG. 2, an openable cover 236 is connected to the top face 116 at one or more locations by a plurality of hinges 210. Even though FIG. 2 shows a plurality of hinges 210, a single hinge 210 is also acceptable. In this embodiment, the openable cover 236 can be opened into an opened position so that, for example, bone grafting material can be inserted into the central compartment 120. The openable cover 236 can also be closed into a closed position. In the closed position, the openable cover 236 can be secured to the top face 116 by one or more latching mechanisms 220. The one or more latching mechanisms 220 can be located generally across from the one or more hinges 210 to secure the openable cover 236 to the frame 110 when the openable cover 236 is in the closed position. The one or more latching mechanisms 220 can be distributed on the top face 116. Even though FIG. 2 shows a plurality of latching mechanisms, one or more latching mechanisms 220 can be acceptably used to secure the openable cover 236 to the cage frame 110. The latching mechanism 220 may be a latch, snap, set-screw, strap, pin, adhesive, or other means known in the art for securing two bodies together. In yet other embodiments, the openable cover 236 is not hinged to top face 116. Instead, the openable cover 236 is set into place and secured to the top face 116 by at least one of the latching mechanisms 220 identified above, but without the use of the one or more hinges 210.

In certain embodiments, the rear face 114 is configured to receive a tool to assist with the insertion of the cage 100. For example, the rear face 114 can have a threaded slot 230 for the attachment of an insertion rod, as shown in FIG. 2. The insertion rod can be used to tap the cage 100 into place with a mallet or hammer.

The cage 100 may be made of any one or a combination of biocompatible materials known in the art that have mechanical properties required for use in interbody inserts. Certain, non-limiting examples of materials include metals, such as titanium and titanium alloys, stainless steel, alloys (including additive manufactured-materials such as titanium-plasma sprayed metals), plastics, such as polyether ether ketone (PEEK), poly(methyl methacrylate) (PMMA), polyethylene (PE), and nylon, and composites, such as carbon fiber. Furthermore, the cage 100 may be formed of a combination of materials, in addition to coatings of materials (e.g., titanium-coated PEEK, PE-coated stainless steel, or the like), or other biocompatible material with suitable mechanical properties.

FIGS. 4 to 8 show another embodiment of an interbody cage 400. The interbody cage 400 is generally similar to the interbody cage 100 in materials, use, and construction. The above-description of, for example, the mesh is, therefore, not repeated. The interbody cage 400 has a frame 410 that extends around the perimeter of the interbody cage 400 and surrounds a central compartment 420. The frame 410 has a vertical face 411, having at least a front face 412, side faces 413, and a rear face 414. Each of the front face 412, the side faces 413, and the rear face 414 may be separated by one or more edges as shown in FIGS. 4 to 8, or they may be configured as one contiguous curved body similar to the embodiments shown in FIGS. 1A and 1C. Alternatively, the vertical face 411 can include a combination of one or more edges and one or more curves. In one embodiment, the front face 412 is configured to substantially fill a gap between the two vertebral bodies such that the front face 412 may have a curvature and thickness greater than a curvature and thickness of rear face 414. Alternatively, the front face 412 may have a curvature and thickness less than a curvature and thickness of rear face 414. In the embodiment shown in FIGS. 4 to 8, the front face 412 and the rear face 414 have substantially the same thickness such that the angle therebetween is approximately 0°. The actual angle will be determined based upon the location of the spinal fusion and the degree necessary for the spinal fusion. The frame 410 can be made of rigid material suitable to withstand the compressive forces of the spine when fully loaded. The side faces 413 can be generally rigid and solid, and can join the front face 412 to the rear face 414.

As seen in FIGS. 4 to 8, at least a portion of the vertical face 411 of frame 410 is open to allow for new bone growth into central compartment 420. In the illustrated embodiment of FIGS. 4 to 8, the vertical face 411 includes a cover 432. The cover 432 can be partially or entirely mesh. The cover 432 can be rigid or it may be flexible to enable additional volume of bone graft material to be placed inside the central compartment 420. Additionally, a cover 434 can be present on a side opposite to the cover 432. The cover 434 can have the same properties as the cover 432, and the cover 434 and 432 can act together to close the top and bottom openings of the central compartment 420. The cover 434 can also be fixed in place to the frame 410, whereas the cover 432 can be inserted into channels in the frame 410. Mechanisms to fix the cover 432 into place in the frame 410 are discussed in other embodiments above, and can be used herein. In other embodiments, the vertical face 411 can be made of a rigid material having one or more larger openings than what is provided by the cover 432. The frame 410 also can have a top face 416 and a bottom face 418. The top face 416 and the bottom face 418 can be generally flat, but may have one or more teeth extending outward from the top face 416 and the bottom face 418, similar to the teeth shown in FIG. 1C.

Figure 5:
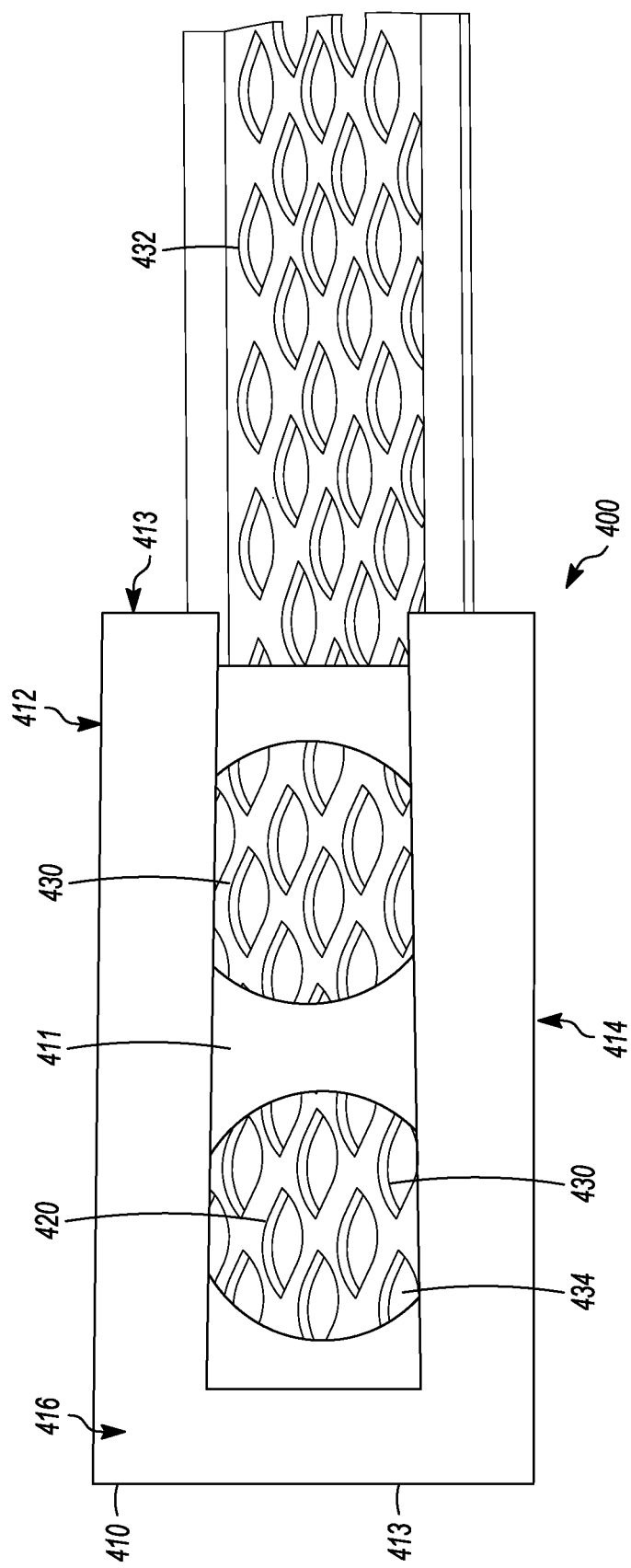
FIG. 5 is a photograph showing a perspective view of the top of the interbody cage of FIG. 4 having a partially open mesh covering, revealing an opening.
Figure 6:
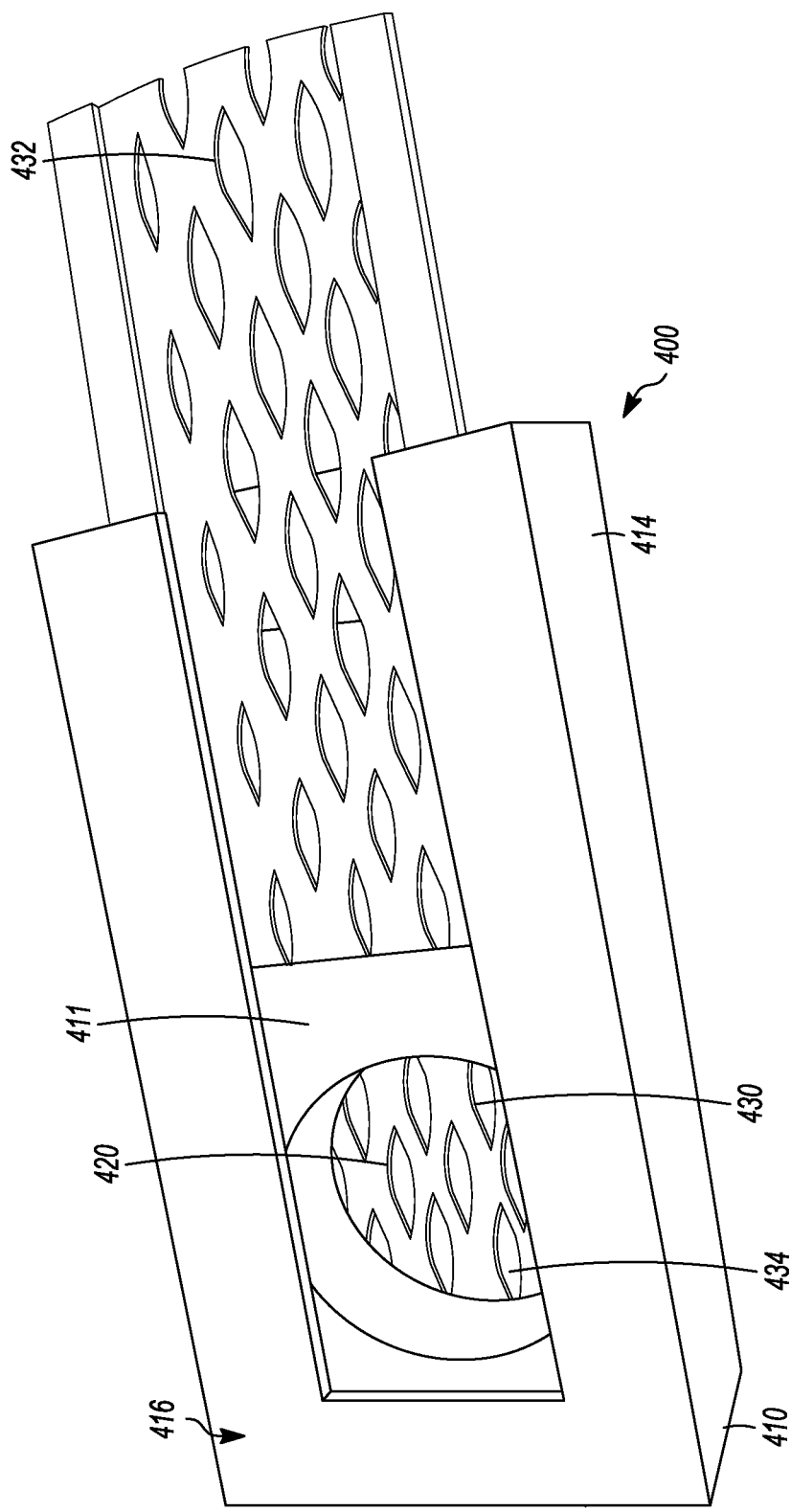
FIG. 6 is a photograph of the top of the interbody cage of FIG. 4 having a fully open mesh covering, revealing two openings.
Figure 7:
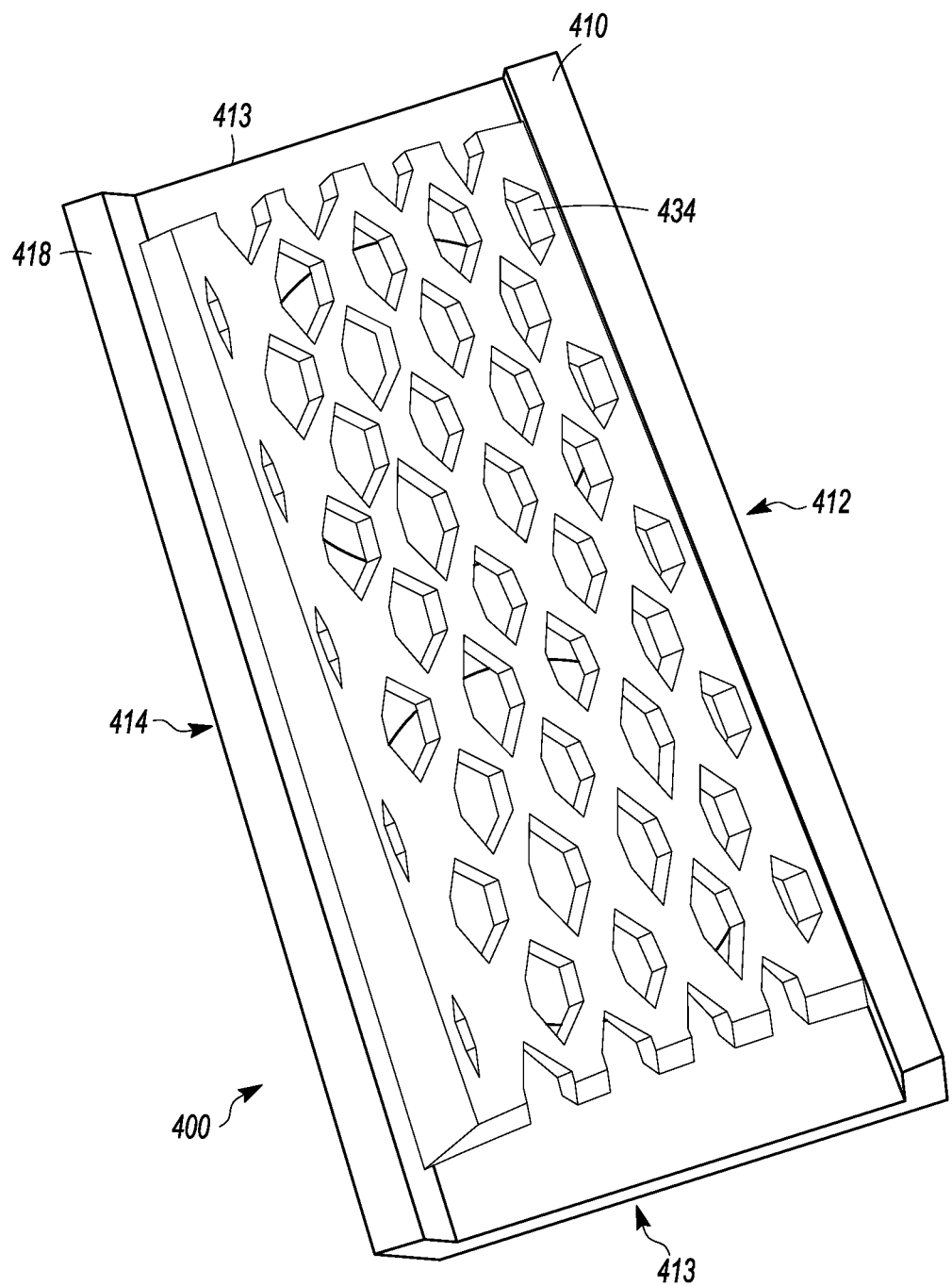
FIG. 7 is a photograph of the bottom of the interbody cage of FIG. 4.
Figure 8:
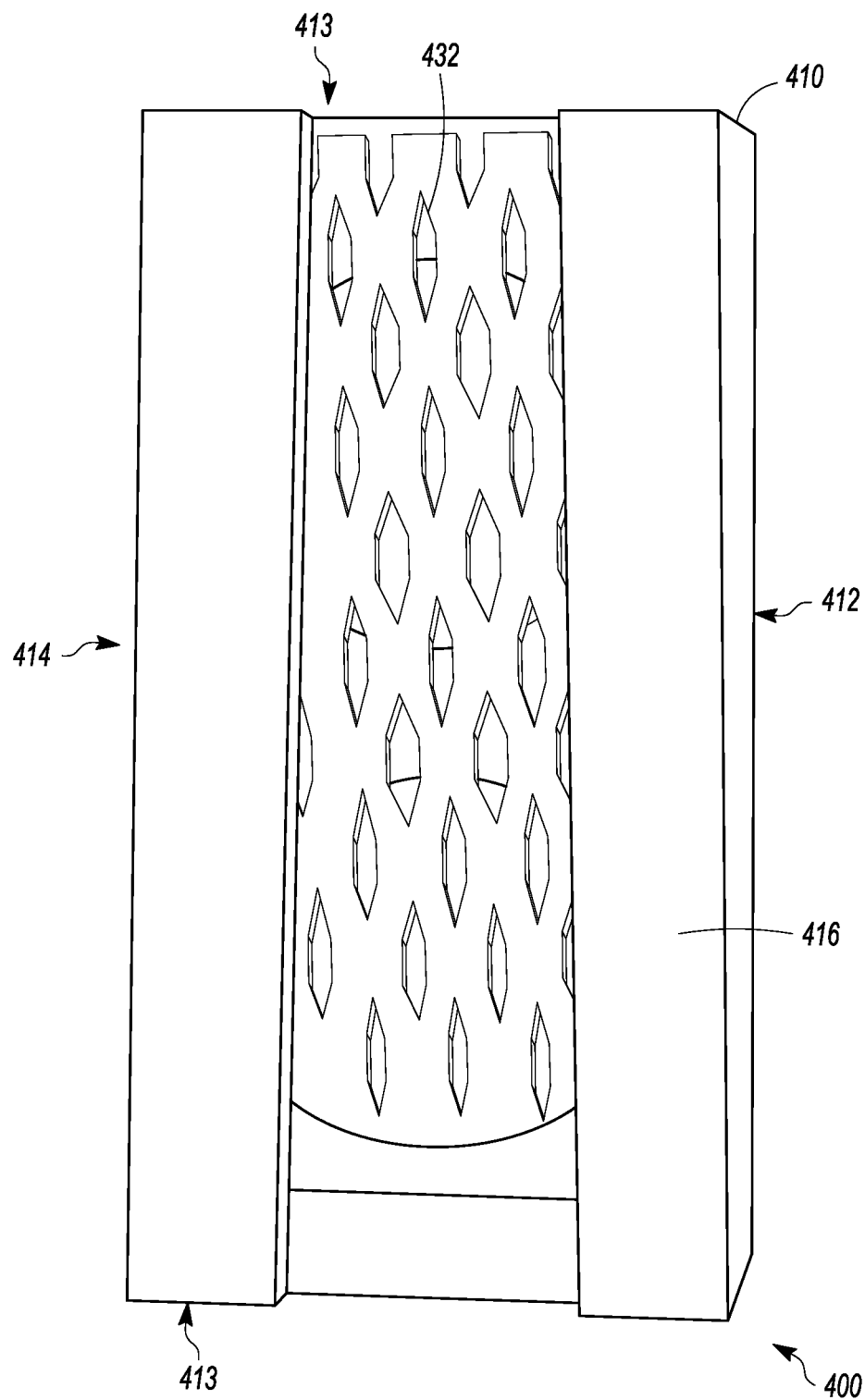
FIG. 8 is a photograph showing a top view of the top of the interbody cage of FIG. 4 having a closed mesh covering.

The top face 416 can have one or more openings 430, as shown in FIG. 5 having two openings, that open the central compartment 420 to the vertebral body above the interbody cage 400. Each of one or more openings 430 can be covered by a cover 432, which can be removable from the interbody cage 400. The cover 432 can have mesh pores that are configured to retain the graft material in the central compartment 420 and to enable bone growth into the middle of the interbody cage 400. The mesh pores can have a diameter that is small enough to retain the graft material within the interbody cage 400 and large enough to allow bone growth through the cover 432 that is mesh.

FIGS. 4 to 6 and 8 show mesh cover 432 may be flat or convex, as described above. The cover 432 can be pliable to frictionally fit into the interbody space. In certain embodiments, the cover 432 can be convex to maximize the amount of graft material that can be packed into central compartment 420. Furthermore, the convex shape of cover 432 can generally flatten when pressure is applied, such as when the weight of the patient compresses the interbody cage 400 when fully loaded between vertebral bodies.

FIGS. 9 to 12 show yet another embodiment of an interbody cage 600. The interbody cage 600 is generally similar to the interbody cage 100 and the interbody cage 400 in materials, use, and construction. The above-description of, for example, the mesh is, therefore, not repeated. The interbody cage 600 has a frame 610 that extends around the perimeter of the interbody cage 600 and surrounds a central compartment 620. Even though the frame 610 has a plurality of edges generally forming a rectangular shape in FIGS. 9 to 12, the frame 610 may also be configured as one contiguous curved body similar to the embodiments shown in FIGS. 1A and 1C or can include a combination of one or more edges and one or more curves.

In an embodiment, the interbody cage 600 is configured to substantially fill a gap between the two vertebral bodies such that the interbody cage 600 may have a curvature and thickness where one side is greater than the other side. In FIGS. 9 to 12, the aforementioned sides have substantially the same thickness such that the angle therebetween is approximately 0°. As mentioned above, the actual angle will be determined based upon the location of the spinal fusion and the degree necessary for the spinal fusion. The frame 610 can be made of rigid material suitable to withstand the compressive forces of the spine when fully loaded.

As seen in FIGS. 9 to 12, at least a portion of the frame 610 is open to allow for new bone growth into central compartment 620. In the illustrated embodiment of FIGS. 4 to 8, the frame 610 includes a cover 632. The cover 632 can be partially or entirely mesh, and may be convex, as discussed in other embodiments above. The cover 632 can be rigid or it may be flexible to enable additional volume of bone graft material to be placed inside the central compartment 620. The frame 610 can also include ridges 612 on the surfaces thereof, but can also or alternatively include different prefabricated textures to facilitate osseointegration.

Figure 9:
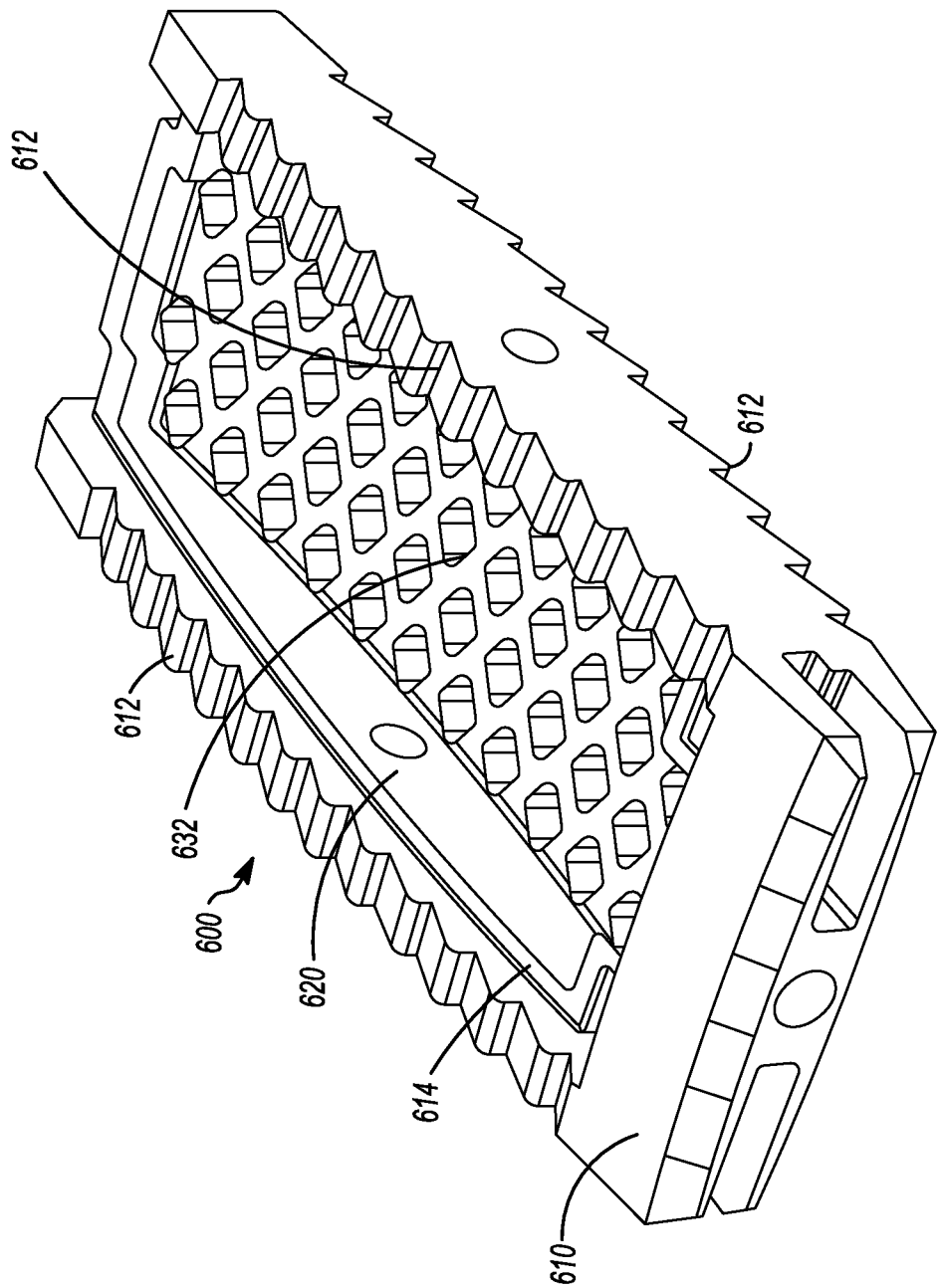
FIG. 9 is a front perspective view of another embodiment of an interbody cage.
Figure 10:
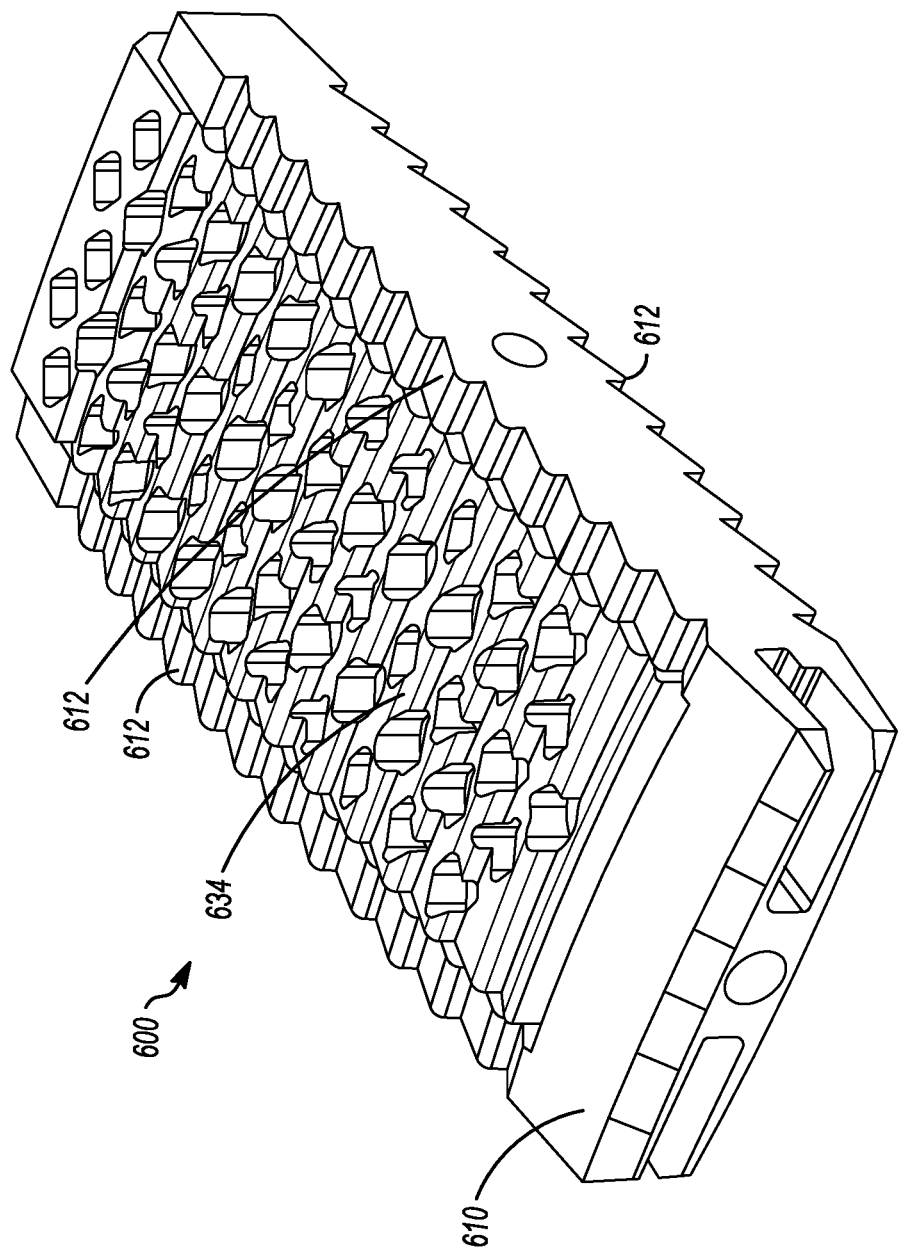
FIG. 10 is a front perspective view of the interbody cage of FIG. 9 having a cover placed thereon.
Figure 11:
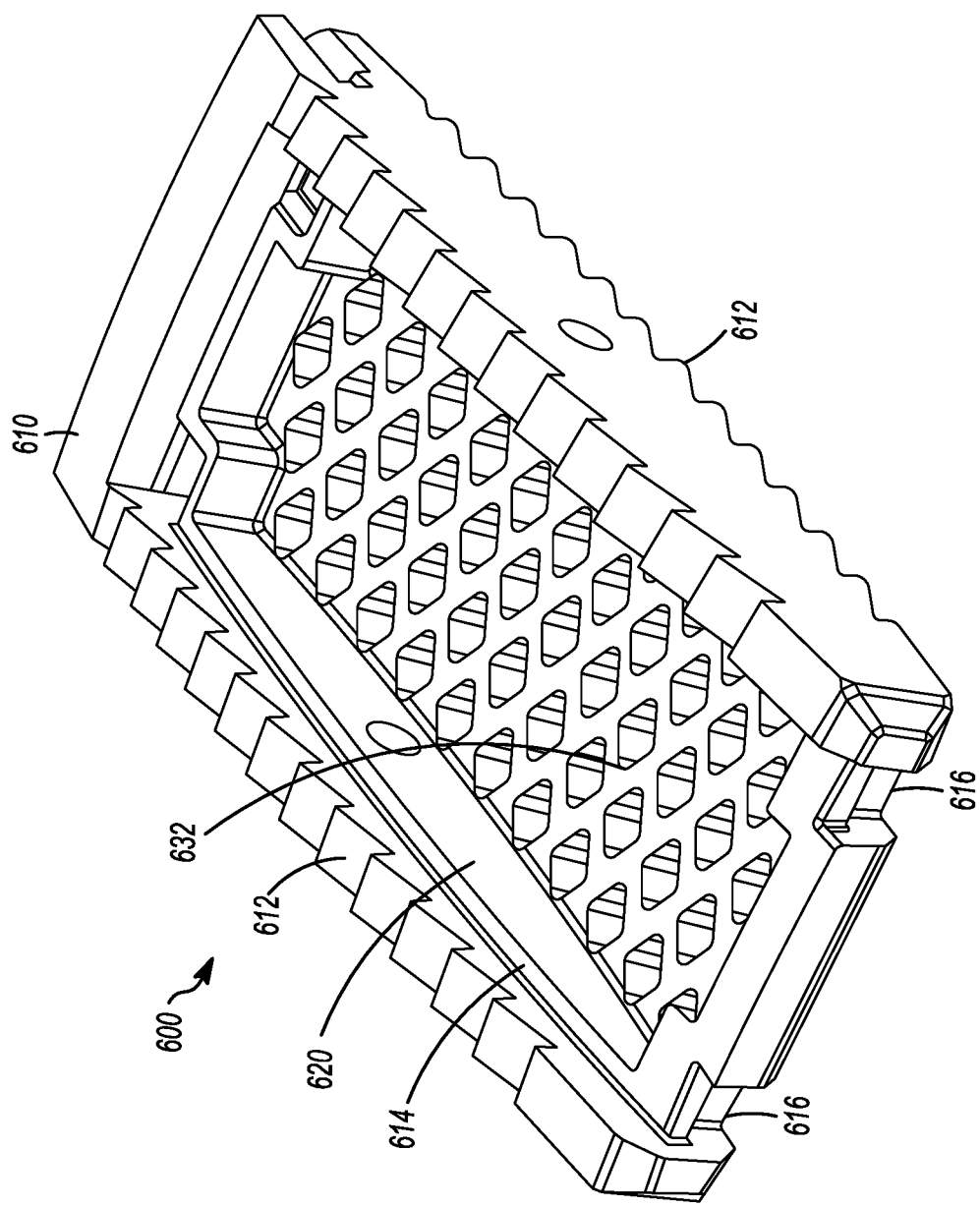
FIG. 11 is a rear perspective view of the interbody cage of FIG. 9
Figure 12:
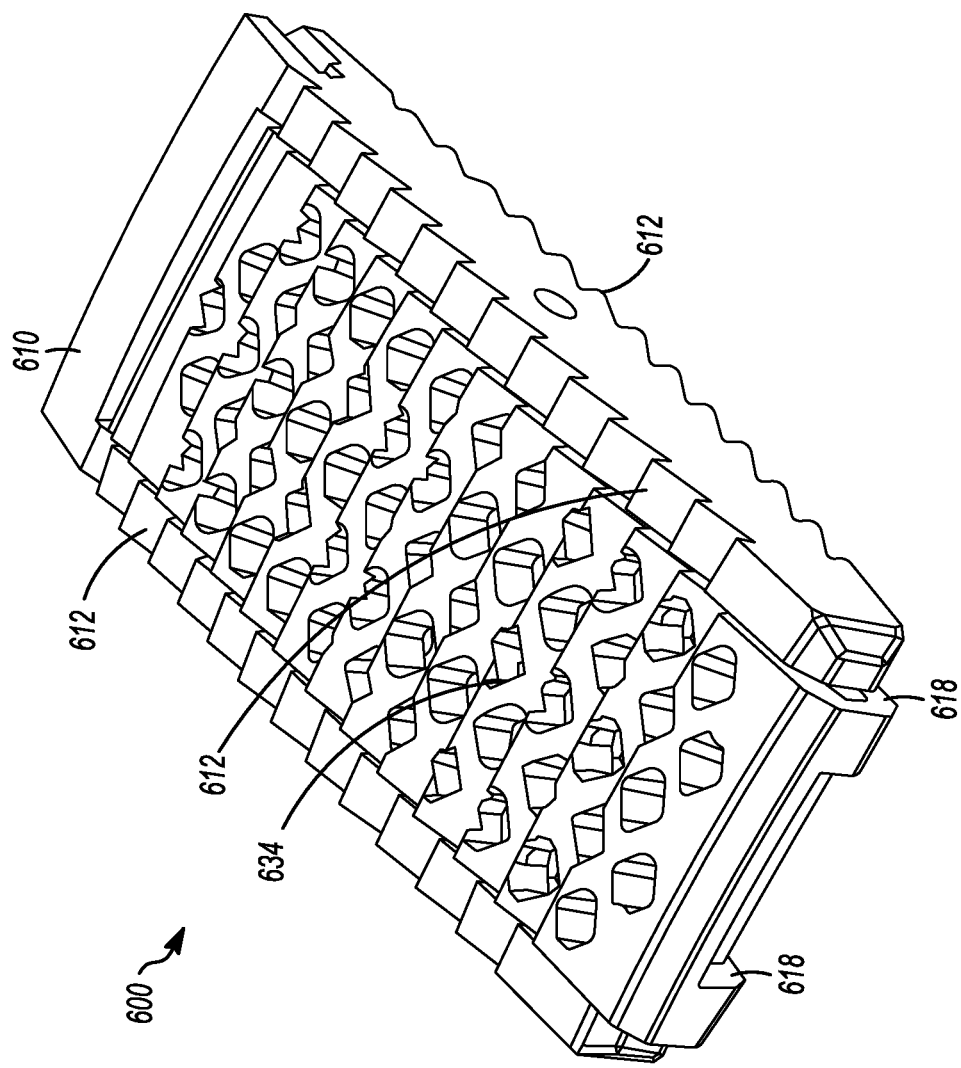
FIG. 12 is a rear perspective view of the interbody cage of FIG. 9 having a cover placed thereon.

Additionally, a cover 634 can be present on a side opposite to the cover 632, as seen in FIG. 10. The cover 634 can have the same properties as the cover 632, and the cover 634 and 632 can act together to close the top and bottom openings of the central compartment 620. The cover 632 can also be fixed in place to the frame 610, whereas the cover 634 can be inserted into channels or placed on grooves 614 in the frame 610, as shown in FIGS. 9 and 11. The cover 634 can engage the frame 610 to be secured to the frame 610 thereby securely enclosing the central compartment 620. The frame 610 can include one or more slots 616 to engage the extensions 618 of the cover 634. When the slots 616 engage the extensions 618, the cover 634 can be secured to the frame 610, as seen in FIGS. 11 and 12. Additional and/or alternative mechanisms to fix the cover 634 to the frame 610 are discussed in other embodiments above, and can be used herein. Also, in certain embodiments, the frame 610 can be configured to receive a tool to assist with the insertion of the interbody cage 600. For example, a threaded slot for the attachment of an insertion rod can be used in a similar manner to those discussed in detail above. The insertion rod can be used to tap the interbody cage 600 into place with a mallet or hammer.

Figure 3:
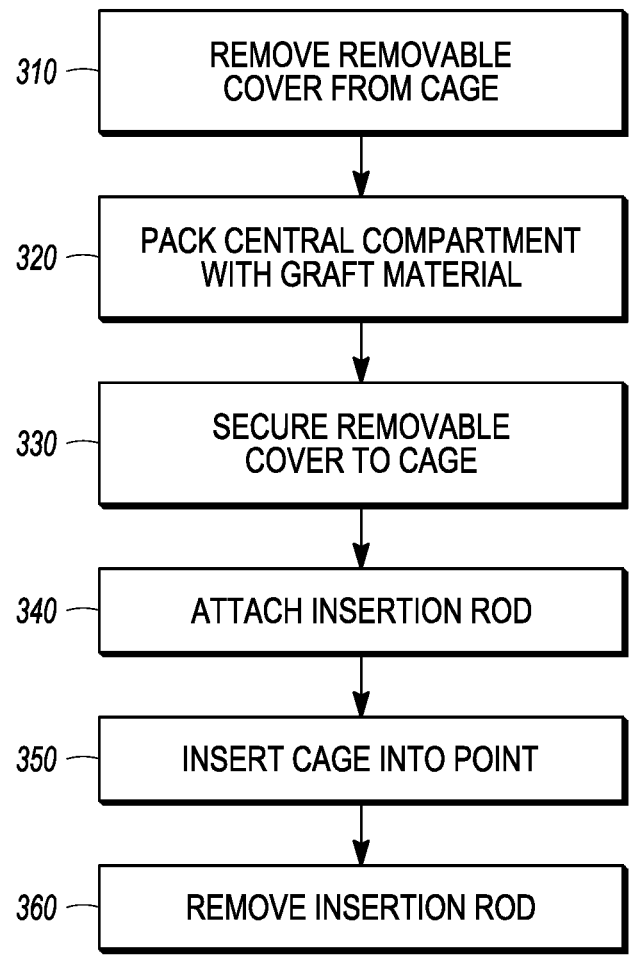
FIG. 3 is a flow chart of a method for installing the interbody cage.
Figure 4:
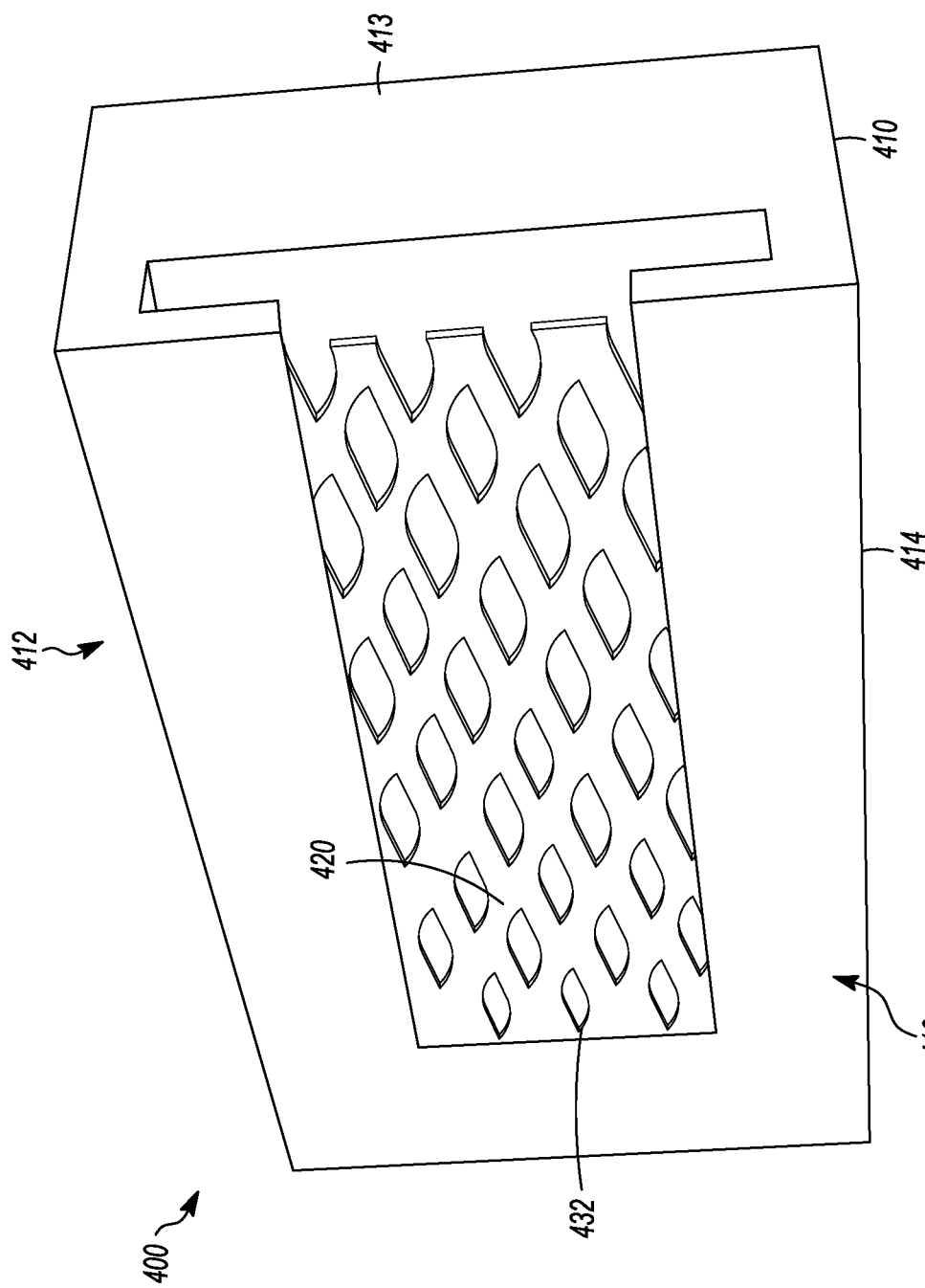
FIG. 4 is a photograph of another embodiment of the interbody cage.

FIG. 3 illustrates flow chart 300 depicting example steps for installing the interbody cages of the present application into a patient, and can be applied to any of the embodiments of the present application. The flow chart 300 is intended to be illustrative of one example method for installing the interbody cage 100. In alternative methods, one or more steps may be omitted or the steps may be performed in a different order. Additional steps may also be added, as needed. In step 310, the cover 134 is removed from the interbody cage 100 so that the central compartment 120 is open to receive grafting material. Next, in step 320, the desired amount of bone grafting material is inserted into the central compartment 120. The desired amount can be determined by the surgeon performing the surgery, but, in general, the central compartment 120 will be filled to the maximum capacity that is possible. Once full, removable mesh covering 134 is slid into channel 136 and is locked into place in step 330. In step 340, the insertion rod is attached to the rear face 114 of interbody cage 100. The interbody cage 100 is then inserted into the intervertebral space by tapping the insertion rod with, for example, a mallet in step 350. In step 360, the insertion rod is removed from the interbody cage 100.

Table 1 illustrates some example dimensions of the interbody cages of the present application. While Table 1 provides exact dimensions, it should be understood that these are illustrative in nature, and do not limit the dimensions of the interbody cages described herein. The exact size of the interbody cages will depend on the physical characteristics of the patient and the location of the spine where the interbody cage will be placed. For example, the footprints of the interbody cages of the present application have a width between approximately 10 mm and 40 mm and a depth of between approximately 15 mm and 75 mm. The interbody cages of the present application may have a height between approximately between 4 mm and 25 mm. The interbody cages of the present application may have a sagittal profile between approximately 0 degrees and 30 degrees.

TABLE 1

| Footprints (mm) | Heights (1 mm increments) | Sagittal Profiles (degrees) of lordosis |
|---|---|---|
| Anterior Lumbar or Thoracic Interbody Fusion Cages | | |
| 20 × 25 | 7-21 mm | 0, 6, 12, 24 |
| 22 × 29 | 7-21 mm | 0, 6, 12, 24 |
| 24 × 35 | 7-21 mm | 0, 6, 12, 24 |
| 28 × 39 | 7-21 mm | 0, 6, 12, 24 |
| Oblique/Lateral Lumbar or Thoracic Interbody Fusion Cages | | |
| 15 wide × 20-25* | 6-18 mm | 0, 6, 8, 12, 24 |
| 17 wide × 40-60* | 6-18 mm | 0, 6, 8, 12, 24 |
| 21 wide × 40-60* | 6-18 mm | 0, 6, 8, 12, 24 |
| 25 wide × 40-60* | 6-18 mm | 0, 6, 8, 12, 24 |

*increments of 5 mm

Further, the interbody cages of present application can be used for cervical fusions. Such interbody cages for cervical fusion include, but are not limited to, two exemplary footprints: (small) 13.5 mm×15.5 mm, and (large) 17.5 mm×15.5 mm. The height of such interbody cages for cervical fusion include, but are not limited to, 4.5, 5.5. 6.5, 7.5, 8.5, 9.5, and 10.5 mm. Also, the sagittal profiles (degrees of lordosis) for such interbody cages for cervical fusion include, but are not limited to, 0 to 7 degrees for the heights of 4.5-7.5 mm and 5-12 degrees for the heights of 5.5 to 10.5 mm.

The angularity of each of the interbody cages of present application will be determined based on typical spinal morphometric analysis of the angularity of the disc space across the cervical-thoraco-lumbar-sacral spine, and thus the above-mentioned angles are provided as non-limited examples. The angularity of each of the interbody cages of present application can be predetermined such that the interbody cages are, manufactured to have a predetermined angle rather than being modified by surgical staff prior to a procedure.

The interbody cages and the associated methods allow biological material, such as bone graft material, to be easily and securely provided while also supporting the spine. Furthermore, the interbody cages can receive biological material, such as bone graft material, without additional special equipment and remain secured when placed into the interbody spinal space.

In the foregoing description, the interbody cages and methods of the present application have been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification, unless the context requires otherwise, the word "comprise" and its variations, such as "comprises" and "comprising," will be understood to imply the inclusion of a stated item, element or step or group of items, elements or steps, but not the exclusion of any other item, element or step or group of items, elements or steps. Furthermore, the indefinite article "a" or "an" is meant to indicate one or more of the item, element or step modified by the article.

The invention claimed is:

1. An interbody cage for spinal stabilization comprising
   a) a frame that surrounds a central compartment, the frame comprising a top face and a bottom face, the top face comprising one or more top openings, and the bottom face comprising one or more bottom openings, wherein the frame has ridges on the top face and ridges on the bottom face,
   b) a cover that covers the one or more bottom openings, the cover comprising mesh suitable for retaining biological material and ridges corresponding to the ridges on the bottom face of the frame, wherein the cover is fixed to the frame, and
   c) an openable cover configured to be secured to the top face of the frame in a closed position and capable of being opened, the openable cover covering the one or more top openings when secured to the top face of the frame in the closed position, the openable cover comprising mesh suitable for retaining biological material, wherein the mesh is convex,
   wherein the frame comprises a plurality of grooves extending along inner walls of the central compartment such that the plurality of grooves are configured to slidably engage and support the openable cover,
   wherein the frame comprises a plurality of slots on an end portion of the frame, the plurality of slots configured to engage a plurality of corresponding extensions on an end portion of the openable cover that corresponds to the end portion of the frame having the plurality of slots, the plurality of slots and the plurality of corresponding extensions securing the openable cover to the frame in the closed position, and
   wherein the openable cover comprises ridges corresponding to the ridges on the top face of the frame when in the closed position.

2. The interbody cage for spinal stabilization of claim 1, wherein the mesh of the cover is convex.

3. The interbody cage for spinal stabilization of claim 1, wherein the mesh of at least one of the cover and the openable cover is flexible mesh.

4. The interbody cage for spinal stabilization of claim 1, wherein the frame is configured to receive an insertion rod.

* * * * *